(12) United States Patent
Liu et al.

(10) Patent No.: US 12,378,187 B1
(45) Date of Patent: Aug. 5, 2025

(54) SELENIUM-CONTAINING NANO HOF, ANTIOXIDANT NANOZYME, PREPARATION METHOD AND APPLICATION THEREOF

(71) Applicant: Hangzhou Normal University, Hangzhou (CN)

(72) Inventors: Junqiu Liu, Hangzhou (CN); Ruizhen Tian, Hangzhou (CN); Yijia Li, Hangzhou (CN); Jiayun Xu, Hangzhou (CN)

(73) Assignee: Hangzhou Normal University, Hangzhou (CN)

( * ) Notice: Subject to any disclaimer, the term of this patent is extended or adjusted under 35 U.S.C. 154(b) by 0 days.

(21) Appl. No.: 18/918,210

(22) Filed: Oct. 17, 2024

(30) Foreign Application Priority Data

Mar. 25, 2024 (CN) .......................... 202410342180.5

(51) Int. Cl.
| | | |
|---|---|---|
| C07C 391/02 | (2006.01) | |
| C07C 257/18 | (2006.01) | |
| C12N 9/02 | (2006.01) | |
| C12N 9/08 | (2006.01) | |

(52) U.S. Cl.
CPC .......... *C07C 391/02* (2013.01); *C07C 257/18* (2013.01); *C12N 9/0065* (2013.01); *C12N 9/0089* (2013.01); *C12Y 111/01006* (2013.01); *C12Y 111/01009* (2013.01); *C12Y 115/01001* (2013.01)

(58) Field of Classification Search
None
See application file for complete search history.

(56) References Cited

FOREIGN PATENT DOCUMENTS

| | | |
|---|---|---|
| CN | 113980035 A | 1/2022 |
| CN | 114099704 A | 3/2022 |

OTHER PUBLICATIONS

Andersson et al. Free Radical Biology & Medicine (1994), 16(1), 17-28 (Abstract) (Year: 1994).*
Ennis et al. Physical Chemistry Chemical Physics (2022), 24(18), 10784-10797(Abstract) (Year: 2022).*
Chen et al. Nat Commun. Aug. 16, 2022;13:4816 (Year: 2022).*
Fang et al. Anal Chem. Sep. 19, 2023;95(37):14143-14149 (Year: 2023).*
Mahbod Morshedi, et al., Mixed halide/oxoanion-templated frameworks, CrystEngComm, 2017, pp. 2367-2371, vol. 19 No. 2367.
Hongqin Jiang, et al., Fluorescent Supramolecular Organic Frameworks Constructed by Amidinium-Carboxylate Salt Bridges, Chem. Eur. J., 2021, pp. 15006-15012, vol. 27.
Ali Z Al-Rubaie, et al., Synthesis, characterization and biological studies of some new organometallic compounds containing mercury, selenium and tellurium based on p-aminobenzoic acid, Journal of Physics: Conference Series, 2021, pp. 1-9, vol. 2063.
Lingshan Gong, et al., A Microporous Hydrogen-Bonded Organic Framework for Efficient Xe/Kr Separation, ACS Appl. Mater. Interfaces, 2022, pp. 19623-19628, vol. 14.
Guo Xin, The Structures, Properties and Nature of Hydrogen, Halogen, Chalcogen and Tetrel Bonds of F2XY, Yantai University, 2016, pp. 1-109.

* cited by examiner

*Primary Examiner* — Christian L Fronda
(74) *Attorney, Agent, or Firm* — Bayramoglu Law Offices LLC (57) ABSTRACT

A multi-enzyme cascade antioxidant nano HOF and preparation method and application thereof are provided. The present invention discloses a nano HOF based on selenium-containing ligand for the first time, the nano HOF does not contain metal and has good biocompatibility, which is a universal loading platform, and has high porosity, acid and alkali resistance and thermal stability, and is size-tunable, it can coat various types of enzymes at the same time, stabilize the conformation of the enzyme through the confinement effect, the high porosity can not only provide enough space for the enzyme, but also facilitate the transport of substances and the play of catalytic properties of the enzyme, 85-90% of the activity of the coated enzyme can be maintained, ROS can be effectively scavenged through the cascade catalysis between various enzymes, which provides a new idea for the construction of bio-friendly antioxidants.

5 Claims, 11 Drawing Sheets

SELENIUM-CONTAINING NANO HOF, ANTIOXIDANT NANOZYME, PREPARATION METHOD AND APPLICATION THEREOF

CROSS REFERENCE TO THE RELATED APPLICATIONS

This application is based upon and claims priority to Chinese Patent Application No. 202410342180.5, filed on Mar. 25, 2024, the entire contents of which are incorporated herein by reference.

TECHNICAL FIELD

The present invention relates to the field of nanozymes preparation technology, particularly to a multi-enzyme cascade antioxidant nano hydrogen-bonded organic framework (HOF) and preparation method and application thereof.

BACKGROUND

Reactive oxygen species (ROS) is a colorless, odorless substance with strong oxidizing properties, and an appropriate concentration of ROS is beneficial to human health: it has a certain antioxidant effect and can remove free radicals in the body, ROS will react with lipids in the cells to produce superoxide ions after entering the human body, which will help to remove free radicals, reduce the damage of free radicals to the body, and delay the speed of cell aging; it can promote cell growth and differentiation, and maintain normal cell function; it can promote blood circulation, and improve cardiovascular and cerebrovascular microcirculation, which can prevent cardiovascular and cerebrovascular diseases to a certain extent; it can also activate the body's immune system and improve the body's immunity, which is conducive to physical health.

However, ultra-physiological concentrations of ROS can induce oxidative stress, cause an imbalance of endogenous antioxidant system, lead to damage of lipids, proteins, deoxyribonucleic acid (DNA), and other biological molecules and disorder of cell signal, and then cause a variety of pathological dysfunction, such as neuropathy, inflammatory rheumatoid arthritis, cancer and so on. Therefore, ROS are used as a therapeutic target to down-regulate abnormal ROS to a level that is compatible with cell biological functions, which has great significance for ensuring cell redox homeostasis, maintaining normal physiological functions of the body, and reducing the incidence of diseases.

Delivering antioxidants directly is an effective way to regulate ROS, and is involved in the regulation of cellular redox status as an exogenous intervention. In early studies, the delivery of conventional non-enzymatic antioxidants is often ineffective in clinical trials of related diseases, while natural enzyme antioxidants also have problems such as poor stability and difficulty in application. Therefore, scientists have prepared nanozymes with similar antioxidant enzyme activity by combining nanotechnology. Nanozymes have the advantages of low cost, large specific surface area, and strong catalytic cycle stability, and have been applied in the treatment of ROS-related diseases. However, nanozymes still have problems such as metal leakage, low catalytic activity, and poor targeting, therefore, the development of nano-antioxidants with bio-friendly, highly catalytically active, and targeting disease sites is of great significance for the treatment of oxidative stress-induced physiological diseases.

SUMMARY

An objective of the present invention is to provide a multi-enzyme cascade antioxidant nano HOF and preparation method and application thereof, so as to provide a metal-free, bio-friendly new carrier that can effectively load natural enzymes and better reserve the catalytic activity of natural enzymes, and the multi-enzyme cascade antioxidant nanozyme prepared by the carrier.

In order to achieve the above objective, the present invention provides a multi-enzyme cascade antioxidant nano HOF and preparation method and application thereof, a nano HOF based on a selenium-containing ligand, a morphology of the nano HOF is a rod-like structure, with a positive charge on a surface, and a size is adjustable, with a size of 10 μm-300 nm; the nano HOF is a hydrogen bond network formed by an amidine-containing compound and carboxyl groups in the selenium-containing ligand, a structural formula of the amidine-containing compound is shown in Formula (I), and a structural formula of the selenium-containing ligand is shown in Formula (II), wherein a R group is one of H—, F—, Br—, OH—, —CH$_3$.

A preparation method for the selenium-containing ligand as described above, the steps are as follows:

1) adding p-aminobenzoic acid and concentrated hydrochloric acid into ultrapure water to mix well, thereby obtaining a hydrochloric acid solution of p-aminobenzoic acid;
2) dissolving sodium nitrite in deionized water, and then slowly adding dropwise into the hydrochloric acid solution of p-aminobenzoic acid prepared in step 1) under a stirring state, and continuing the reaction for 5-10 min after the completion of the dropwise addition, thereby obtaining a clear pale yellow solution;
3) adding the ultrapure water to a mixture of selenium powder and sodium borohydride under a protection of nitrogen, slowly adding the clear pale yellow solution obtained in step 2) into the solution after no bubbles are generated, and continuing the reaction for 3-4 h after the completion of the dropwise addition;

4) after completing the reaction, adding the concentrated hydrochloric acid dropwise to the solution until the yellow solid is no longer precipitated, filtering, and taking precipitate, obtaining a crude product of selenium-containing ligand after washing with the ultrapure water and drying, and obtaining the selenium-containing ligand represented by formula (II) after purifying the crude product.

Preferably, in step 1), a mass volume ratio of p-aminobenzoic acid:concentrated hydrochloric acid:ultrapure water is 2.5 g:1 mL:1 mL; in step 2), a mass volume ratio of sodium nitrite:deionized water is 0.3 g:1 mL, and the slowly adding dropwise is added at an interval of 5 s/drop; in step 3), a mass ratio of selenium powder:sodium borohydride is 5:17.

A preparation method for nano HOF based on the selenium-containing ligand as described above, the steps are as follows:

S1, preparing an amidine-containing compound solution with a certain concentration, then adding the prepared selenium-containing ligand solution under a condition of mechanical stirring at a room temperature, and obtaining a selenium-containing nano HOF solution after stirring well;

S2, centrifuging and washing the selenium-containing nano HOF solution prepared in step S1 at a low temperature for several times, and then drying the solution in a vacuum drying oven, thereby obtaining nano HOF powder based on the selenium-containing ligand.

Preferably, in step S1, the selenium-containing ligand solution is an alkaline solution, which is one or two of sodium hydroxide solution and ammonia solution, a solution pH is 10-12, and a molar ratio of the amidine-containing compound to the selenium-containing ligand is 5-1:1, the selenium-containing ligand nano HOF with different sizes is obtained by adjusting the molar ratio of the amidine-containing compound to the selenium-containing ligand; in step S2, the low temperature refers to 4° C., and washing refers to washing with ultrapure water.

An application for nano HOF based on the selenium-containing ligand as described above in a preparation of antioxidant nanozymes, in the application, the nano HOF based on selenium-containing ligand is used as a loading platform, and the enzyme is a natural antioxidant enzyme or enzyme-like activity small molecules, peptides, and inorganic nanoparticles.

A multi-enzyme cascade antioxidant nanozyme prepared by nano HOF based on the selenium-containing ligand as described above.

A preparation method for the multi-enzyme cascade antioxidant nanozyme as described above, the steps are as follows:

successively adding the amidine-containing compound solution and a prepared natural enzyme solution under a condition of mechanical stirring at room temperature; after stirring for a period of time, then adding the prepared selenium-containing ligand solution, and obtaining an antioxidant nanozyme solution after a full stirring; centrifuging and washing the above-mentioned antioxidant nanozyme solution for several times at low temperature, and then drying in the vacuum drying oven, thereby obtaining antioxidant nanozyme powder.

Preferably, the natural enzyme solution is one or two of glutathione peroxidase, catalase, and superoxide dismutase, and a loading amount in the system is 5-10 wt %; stirring for a period of time refers to stirring for 10-15 min, the centrifuging and washing at low temperature refers to centrifugation at 5000 RPM for 8-10 min at 4° C., and washing with ultrapure water for 3-5 times.

An application for the multi-enzyme cascade antioxidant nanozyme as described above in reducing a concentration of ROS.

Therefore, the present invention provides a multi-enzyme cascade antioxidant nano HOF and preparation method and application thereof, the specific technical effects are as follows:

(1) the present invention discloses a nano HOF based on selenium-containing ligand for the first time, the nano HOF does not contain metal and has good biocompatibility, which is a universal loading platform; the carboxyl group and the amidine group in the selenium-containing ligand can quickly form a hydrogen bond interpenetrating network, the formed hydrogen bond skeleton has high porosity, and has acid and alkali resistance and thermal stability; the structure size of the nano HOF can be controlled by adjusting the ratio between the amidine-containing compound and the selenium-containing ligand, which is more conducive to biological applications;

(2) the preparation method for selenium-containing nano HOF provided by the present invention can also coat a variety of natural enzymes at the same time during the formation process to construct an antioxidant system with a cascade of artificial enzymes and natural enzymes, this system has the following advantages: 1) the ultra-high porosity of HOF can provide enough space for natural enzymes; 2) the tightly surrounded HOF layer stabilizes the conformation of the enzyme through a confinement effect; 3) the porous network structure is beneficial to the material transport and the play of catalytic properties of the enzyme;

(3) the multi-enzyme cascade antioxidant nanozyme based on selenium-containing nano HOF provided by the present invention has good biocompatibility, through the cascade catalysis between superoxide dismutase, glutathione peroxidase and catalase, it can effectively scavenge ROS and reduce the damage of excessive ROS to cells, provide a new idea for the construction of bio-friendly antioxidants and provides a new paradigm for the treatment of related diseases induced by continuous oxidative stress.

Further detailed descriptions of the technical scheme of the present invention can be found in the accompanying drawings and embodiments.

BRIEF DESCRIPTION OF THE DRAWINGS

To explain the embodiments of the present invention or the technical solutions in the prior art more clearly, a brief introduction will be made to the accompanying drawings used in the embodiments. It is obvious that the drawings in the description below are only some embodiments of the present invention, and those ordinarily skilled in the art can obtain other drawings according to these drawings without creative work.

FIGS. 6A-6D are scanning electron microscope images of four kinds of selenium-containing nano HOF aqueous solution in the experimental test 2 of the present invention, wherein

DETAILED DESCRIPTION OF THE EMBODIMENTS

The technical solution of the present invention will be further elaborated hereafter in conjunction with accompanying drawings and embodiments.

In order to make the objectives, the technical solutions, and the advantages of the application more clear, thorough and complete, the technical scheme of the present invention is described clearly and completely through the attached drawings and embodiments. The following detailed descriptions are descriptions of the embodiments, aiming to provide further detailed descriptions of the present invention. Unless otherwise specified, all technical terms used in the present invention have the same meaning as those commonly understood by the general technical personnel in the field to which the application belongs.

The instruments and reagents used in the embodiments are all commercially available.

Embodiment 1

The preparation for amidine-containing compound as shown in Formula (I), the specific steps are as follows:

S1.1, 10.17 g of copper cyanide and 13.63 g of tetrakis (4-bromophenyl) methane were added into 80 mL of N, N-Dimethylformamide (DMF) and reacted at 140° C. for 48 h under a nitrogen atmosphere.

S1.2, after the reaction, DMF was spin-dried, and extracted with dichloromethane, and then washed with 1 mM of sodium ethylenediaminetetraacetate aqueous solution and saturated salt water, respectively. The organic layer was dried by anhydrous magnesium sulfate, and after filtration and evaporation, the obtained crude product was purified by column chromatography to obtain a white solid.

S1.3, the 0.5 g of white solid obtained by step S1.2 was dissolved in 10 mL of dry tetrahydrofuran (THF), cooled to −78° C. with liquid nitrogen under the protection of nitrogen, and then THF solution of the lithium bis(trimethylsilyl) amide (LiHMDS) (7.1 mL, 1.0 M) was added dropwise, and the precipitate was obtained immediately. The mixture was placed at room temperature, stirred overnight, and the precipitate was slowly dissolved to obtain an orange solution.

Figure 1:
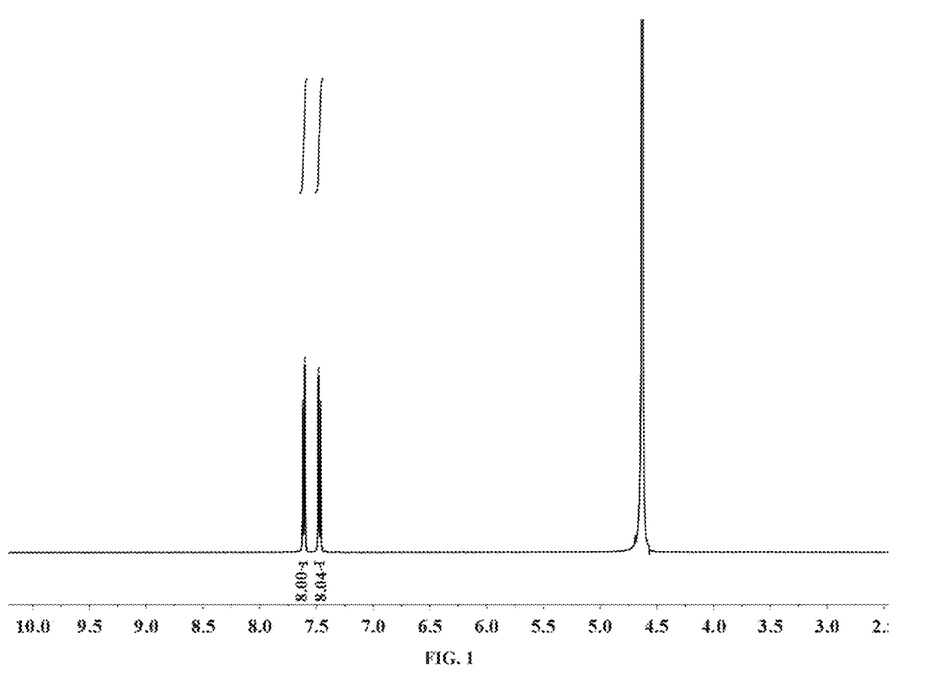
FIG. 1 is a nuclear magnetic resonance hydrogen spectrum of amidine-containing compound prepared by embodiment 1 of the present invention.

After the above solution was cooled to 0° C., 12 mL of liquid (2 mL of acetyl chloride and 10 mL of ethanol) was added to form a grayish-white precipitate. Amidine-containing compound can be obtained as shown in Formula (I) after filtered, fully washed with anhydrous ethanol, and vacuum dried, the nuclear magnetic resonance hydrogen spectrum of amidine-containing compound is shown in FIG. 1.

Embodiment 2

The preparation for selenium-containing ligand as shown in Formula (II), the specific steps are as follows:

S2.1, 2.5 g of p-aminobenzoic acid and 1 mL of concentrated hydrochloric acid were added to a round-bottom flask containing 3 mL of water, and mixed well to obtain a hydrochloric acid solution of p-aminobenzoic acid. The 0.6 g of sodium nitrite was dissolved in 2 mL of water, and then added dropwise to the prepared hydrochloric acid solution of p-aminobenzoic acid at the rate of 5 s/drop, after dropping, the reaction was continued for 5 min to obtain a clear pale yellow solution.

Figure 2:
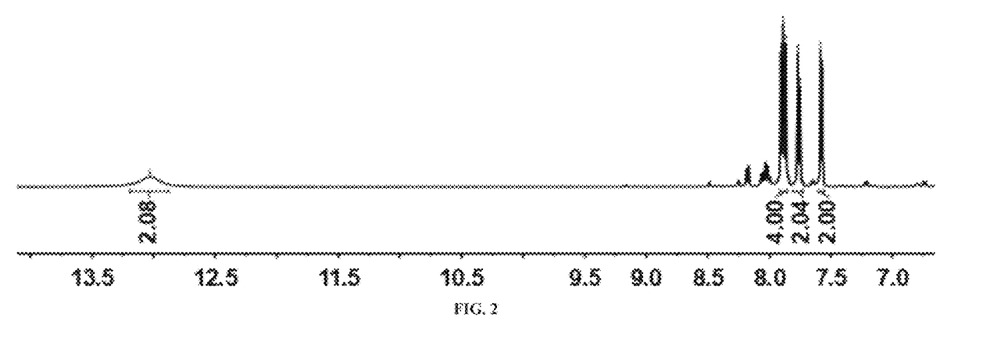
FIG. 2 is a nuclear magnetic resonance hydrogen spectrum of selenium-containing ligand prepared by embodiment 2 of the present invention.

S2.2, 0.5 g of selenium powder and 1.7 g of sodium borohydride were added to the round-bottom flask, and 5 mL of water was added under the protection of nitrogen, after no bubbles were generated, the clear yellow solution obtained by step S2.1 was slowly added dropwise, the reaction was continued for 4 h after dropped. After the reaction, concentrated hydrochloric acid was added dropwise to the solution until the yellow solid no longer precipitate, filtered, and the precipitate was taken, the selenium-containing ligand can be obtained as shown in Formula (II) after washed with ultrapure water, dried, and purified by column chromatography, the structural formula is (II)

the nuclear magnetic resonance hydrogen spectrum of selenium-containing ligand is shown in FIG. 2.

Embodiment 3

The amidine-containing compound prepared by embodiment 1 and the selenium-containing ligand prepared by embodiment 2 were used to prepare the selenium-containing ligand nano HOF, the specific steps are as follows:

S3.1, 10 mg of the amidine-containing compound shown in Formula (I) prepared by embodiment 1 was added to 10 mL of deionized water and stirred for 5 min to obtain an amidine-containing compound solution.

S3.2, 1.5 mg of selenium-containing ligand shown in Formula (II) prepared by embodiment 2 was dissolved in 2 mL of deionized water, and then the pH of the solution was adjusted to 10 with 2M of sodium hydroxide solution to obtain selenium-containing ligand solution.

Figure 3:
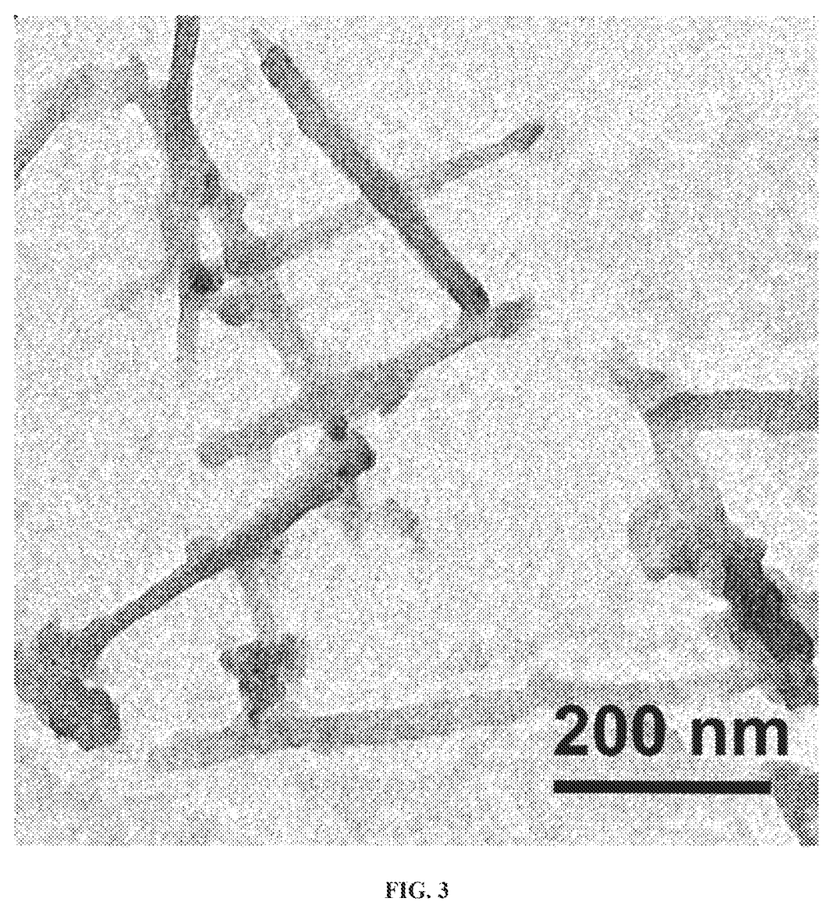
FIG. 3 is a scanning electron microscope image of nano HOF based on selenium-containing ligand prepared by embodiment 3 of the present invention.
Figure 4:
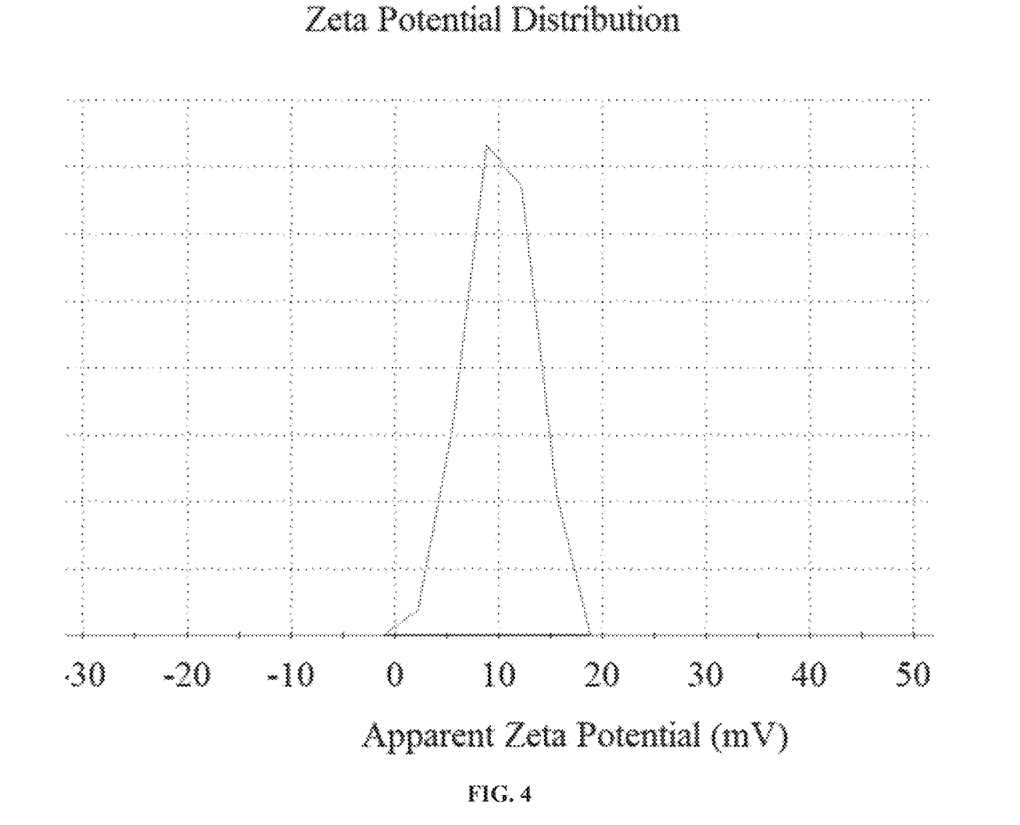
FIG. 4 is an apparent zeta potential diagram of nano HOF based on selenium-containing ligand prepared by embodiment 3 of the present invention.

S3.3, under the condition of 20° C. and stirred, the selenium-containing ligand solution prepared by step S3.2 was added dropwise to the amidine-containing compound solution prepared by step S3.1 at a rate of 10 s/drop, after stirring for 2 h, it was centrifuged at 5000 RPM for 10 min at 4° C., and washed with ultrapure water for 3 times, the precipitate was redispersed into ultrapure water to obtain a selenium-containing nano HOF aqueous solution, the scanning electron microscope image is shown in FIG. 3, and the apparent zeta potential was tested by a Malvern nanoparticle size analyzer, the results are shown in FIG. 4.

It can be seen from FIG. 3 and FIG. 4 that the synthesized nano HOF has a rod-like structure of about 300 nm, and its apparent zeta potential is about +10 mV.

Experimental Test 1

The glutathione peroxidase (GPx) activity test is carried out for nano HOF based on the selenium-containing ligand prepared in embodiment 3, the specific steps are as follows:

S4.1, the GPx activity was measured by coupling reductase method, the mixture solution containing 50 mM of phosphate buffer (pH7.4, 1.0 mM of ethylenediaminetetraacetic acid (EDTA)), 1.0 U·mL$^{-1}$ of glutathione reductase (GR), 1.0 mM of glutathione (GSH) and different concentrations of selenium-containing nano HOF aqueous solution (concentrations were 0.259 μg/mL, 0.518 μg/mL, 0.777 μg/mL, 1.036 μg/mL, 1.295 μg/mL, and 2.590 μg/mL, respectively) was incubated at 37° C. for 3 min, and then 0.25 mM of nicotinamide adenine dinucleotide phosphate (NADPH) solution was added, and continued to incubate for 1 min. Finally, 0.5 mM of $H_2O_2$ was added to start the reaction.

Figure 5:
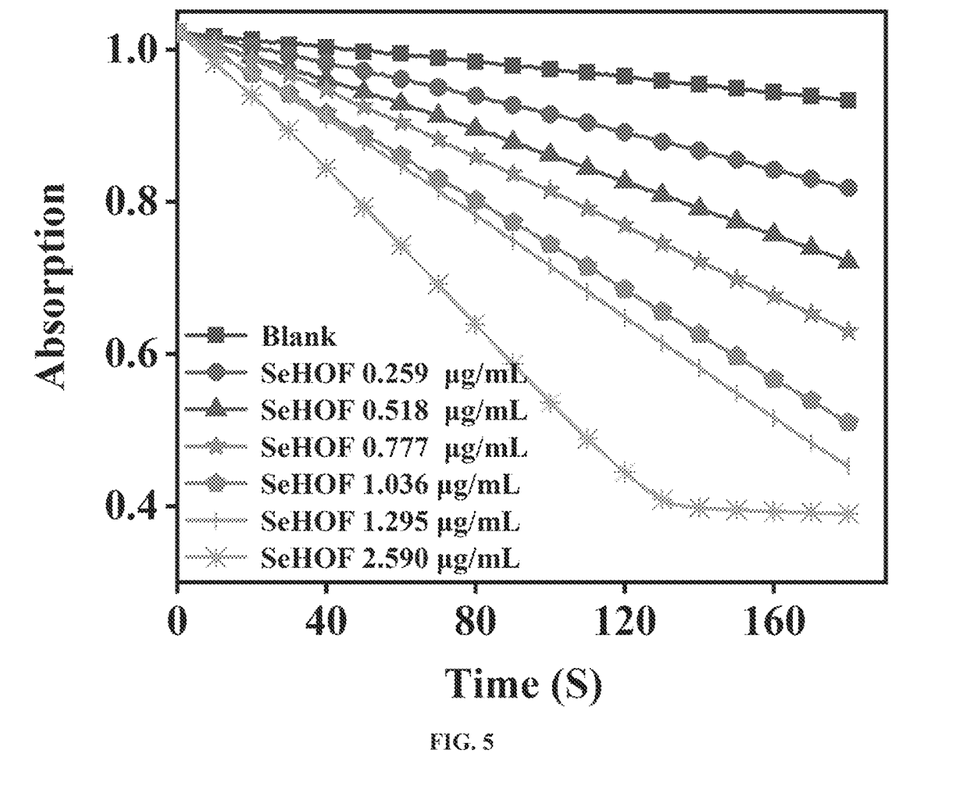
FIG. 5 is a result of glutathione peroxidase activity test of nano HOF based on selenium-containing ligand in embodiment 4 of the present invention.

S4.2, the absorption value of NADPH at 340 nm (F=6220M$^{-1}$ cm$^{-1}$, pH=7.4) was measured by using an ultraviolet/visible spectrophotometer, and the GPx activity was determined according to the change of the absorption value, the absorption value is shown in FIG. 5.

It can be seen from FIG. 5 that with the increase of the concentration of selenium-containing nano HOF, the activity of GPx is also gradually enhanced, and the selenium-containing nano HOF exhibits a concentration-dependent characteristic of the enzyme, indicating that the selenium-containing nano HOF has good glutathione peroxidase activity.

Experimental Test 2

The size tunability of nano HOF based on the selenium-containing ligand prepared in embodiment 3 was investigated, the specific steps are as follows:

S5.1, 1 mg, 2 mg, 5 mg, and 10 mg of amidine-containing compounds shown in Formula (I) prepared by embodiment 1 were added to 10 mL of deionized water respectively, and stirred for 5 min, the amidine-containing compound solutions with four concentrations of 0.1 mg/mL, 0.2 mg/mL, 0.5 mg/mL, and 1 mg/mL were obtained.

S5.2, the 6 mg of selenium-containing ligand shown in Formula (II) prepared by embodiment 2 was dissolved in 8 mL of deionized water, and then the solution pH was adjusted to 10 with 2M of sodium hydroxide solution to obtain a selenium-containing ligand solution.

Figure 6A:
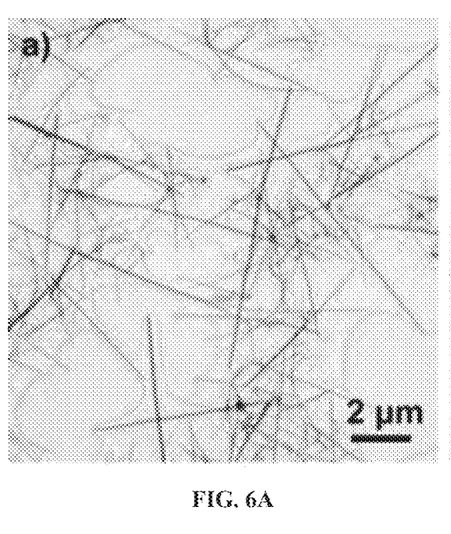
FIG. 6A is a scanning electron microscope image of selenium-containing nano HOF aqueous solution prepared by 0.1 mg/mL of amidine-containing compound solution.
Figure 6B:
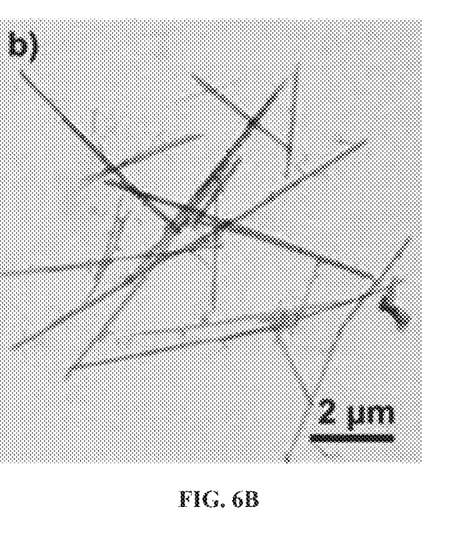
FIG. 6B is a scanning electron microscope image of selenium-containing nano HOF aqueous solution prepared by 0.2 mg/mL of amidine-containing compound solution.
Figure 6C:
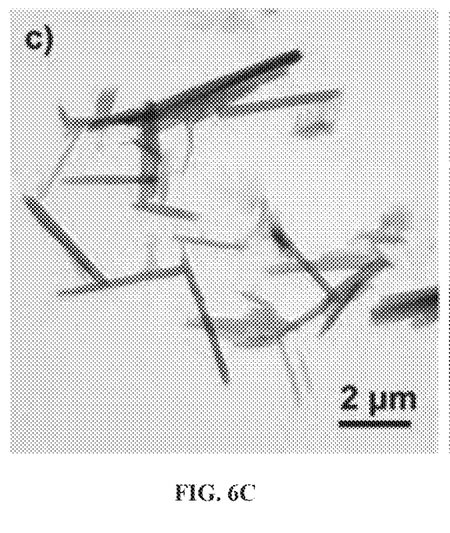
FIG. 6C is a scanning electron microscope image of selenium-containing nano HOF aqueous solution prepared by 0.5 mg/mL of amidine-containing compound solution.
Figure 6D:
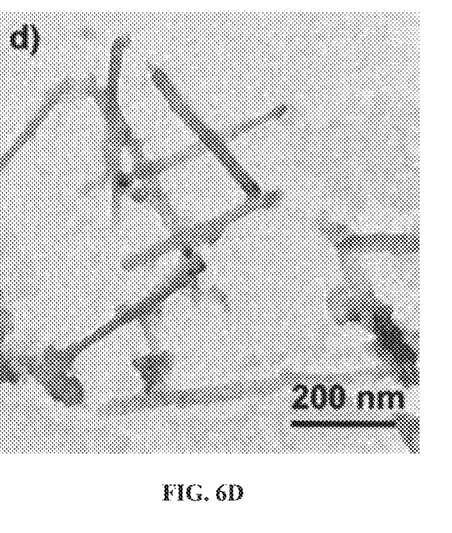
FIG. 6D is a scanning electron microscope image of selenium-containing nano HOF aqueous solution prepared by 1 mg/mL of amidine-containing compound solution.

S5.3, under the condition of 20° C. and stirring, 2 mL of selenium-containing ligand solution prepared by step S5.2 was added dropwise to the four concentrations of amidine compound solution prepared by step S5.1 at a rate of 10 s/drop, after stirring for 2 h, it was centrifuged at 5000 RPM for 10 min at 4° C., and washed with ultrapure water for 3 times, the precipitate was redispersed into ultrapure water to obtain four selenium-containing nano HOF aqueous solutions, the scanning electron microscope image of four kinds of selenium-containing nano HOF aqueous solution are shown in FIGS. 6A-6D, wherein FIG. 6A is a scanning electron microscope image of selenium-containing nano HOF aqueous solution prepared by 0.1 mg/mL of amidine-containing compound solution; FIG. 6B is a scanning electron microscope image of selenium-containing nano HOF aqueous solution prepared by 0.2 mg/mL of amidine-containing compound solution; FIG. 6C is a scanning electron microscope image of selenium-containing nano HOF aqueous solution prepared by 0.5 mg/mL of amidine-containing compound solution; FIG. 6D is a scanning electron microscope image of selenium-containing nano HOF aqueous solution prepared by 1 mg/mL of amidine-containing compound solution.

It can be seen from FIGS. 6A-6D that the size of selenium-containing nano HOF prepared by 0.1 mg/mL of amidine-containing compound solution is about 10 m, the size of selenium-containing nano HOF prepared by 0.2 mg/mL amidine-containing compound solution is about 6 m, the size of selenium-containing nano HOF prepared by 0.5 mg/mL amidine-containing compound solution is about 3 m, and the size of selenium-containing nano HOF prepared by 1 mg/mL amidine-containing compound solution is about 300 nm. It is shown that applying the nano HOF based on selenium-containing ligand prepared by the method provided by the present invention is size-tunable.

Embodiment 4

A multi-enzyme cascade loaded superoxide dismutase nanozyme based on selenium-containing nano HOF was prepared, the specific steps are as follows:

S5.1, 10 mg of the amidine-containing compound shown in Formula (I) prepared by embodiment 1 was added to 10 mL of deionized water and stirred for 5 min to obtain an amidine-containing compound solution. A superoxide dismutase solution was prepared by dissolving 0.1 mg of superoxide dismutase in 1 mL of ultrapure water.

S5.2, 1.5 mg of selenium-containing ligand shown in Formula (II) prepared by embodiment 2 was dissolved in 2 mL of deionized water, and then the pH of the solution was adjusted to 10 with 2M of sodium hydroxide solution to obtain selenium-containing ligand solution.

S5.3, under the condition of 20° C. and stirred, the enzyme solution was added dropwise to the solution containing amidine compound prepared by step S5.1 at the rate of is/drop, after stirring for 10 min, the selenium-containing ligand solution was added dropwise at the rate of 10 s/drop, after stirring for 2 h, it was centrifuged at 5000 RPM for 10 min at 4° C., and washed with ultrapure water for 3 times, the precipitate was redispersed into ultrapure water to obtain a multi-enzyme cascade antioxidant nanozyme aqueous solution, which was recorded as SeHOF@SOD.

Embodiment 5

A multi-enzyme cascade nanozyme loaded catalase based on selenium-containing nano HOF was prepared, the method was exactly the same as that of Embodiment 4, only the added enzyme was catalase, and the obtained multi-enzyme cascade antioxidant nanozyme aqueous solution was recorded as SeHOF@CAT.

Embodiment 6

A multi-enzyme cascade nanozyme loaded superoxide dismutase and catalase based on selenium-containing nano HOF was prepared, the method was the same as that of Embodiment 4, only the added enzymes were superoxide dismutase and catalase, the additional amount of superoxide dismutase and catalase was 0.1 mg, and the obtained multi-enzyme cascade antioxidant nanozyme aqueous solution was recorded as SeHOF@CAT@SOD.

Figure 7:
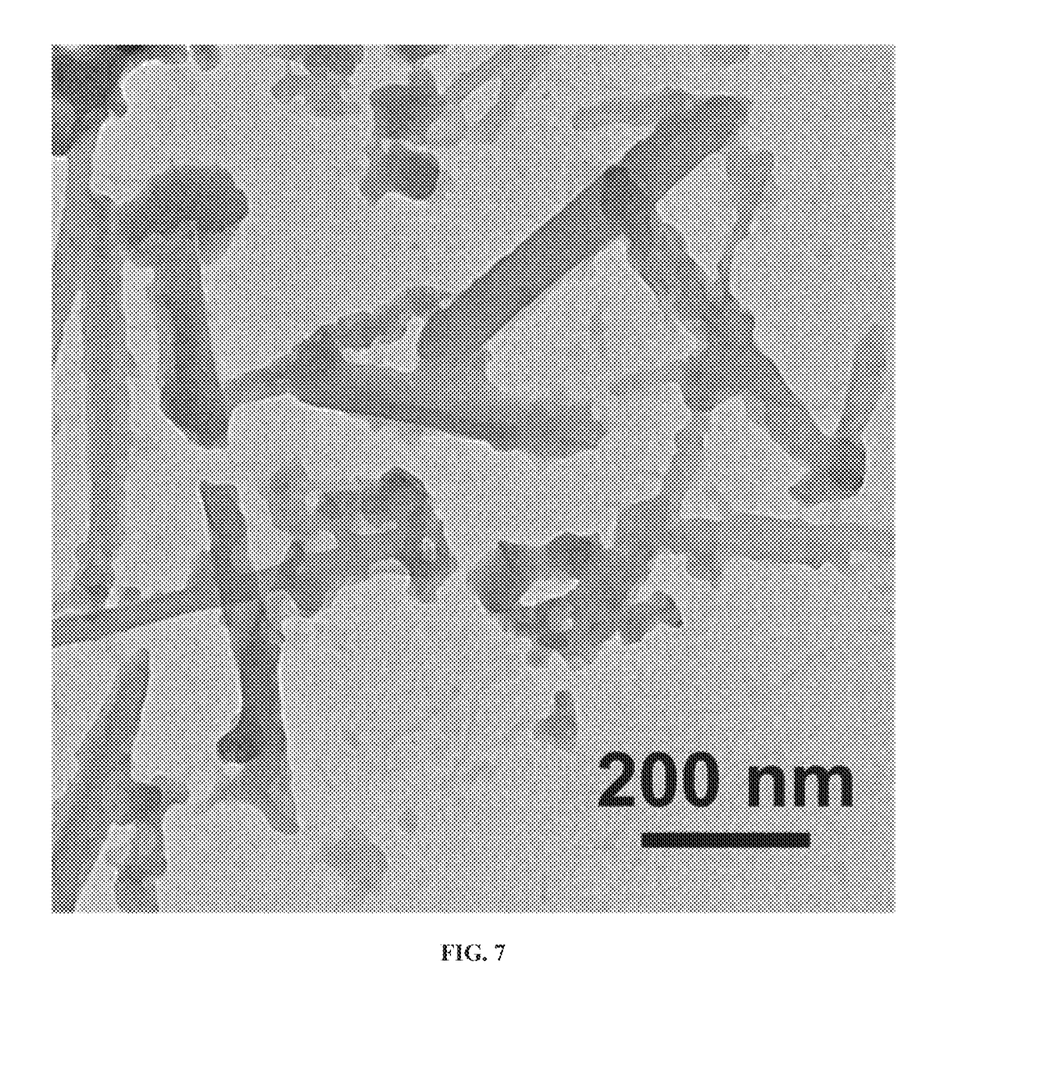
FIG. 7 is a scanning electron microscope image of a multi-enzyme cascade antioxidant nanozyme based on the selenium-containing ligand nano HOF prepared by embodiment 6 of the present invention.

The scanning electron microscope image is shown in FIG. 7, after the selenium-containing nano HOF is loaded with superoxide dismutase and catalase, the rod-like structure is still maintained, and its size is about 300 nm, which proves the successful construction of multi-enzyme cascade antioxidant nanozymes.

Experimental Test 3

The superoxide dismutase activity test of the multi-enzyme cascade antioxidant nanozyme prepared in embodiment 4 was tested, the steps are as follows:

SOD activity was quantified by using a standard xanthine/xanthine oxidase (XOD) assay system developed by McCord and Fridovich. The xanthine/XOD system produced superoxide radical anion at pH=7.0 (phosphate buffer, 25° C.). Appropriate amount of antioxidant nanozyme (0.248 µg/mL, 0.645 µg/mL, 1.24 µg/mL, 2.48 µg/mL, 4.96 µg/mL, and 12.4 µg/mL) was added to an aqueous solution containing XOD (final concentration is 0.025 U·mL$^{-1}$), 100 mM of nitro blue tetrazolium (NBT), 300 mM of xanthine, 0.1 mM of EDTA and 50 mM of phosphate buffer (final volume is 500 µL) and the oxidation of the water-soluble tetrazolium salt WST-8 was monitored at 450 nm using a UV/Vis spectrophotometer. SOD activity was evaluated by using the enzyme concentration at which the oxidation rate of WST-8 was inhibited by 50% (IC$_{50}$).

Figure 8:
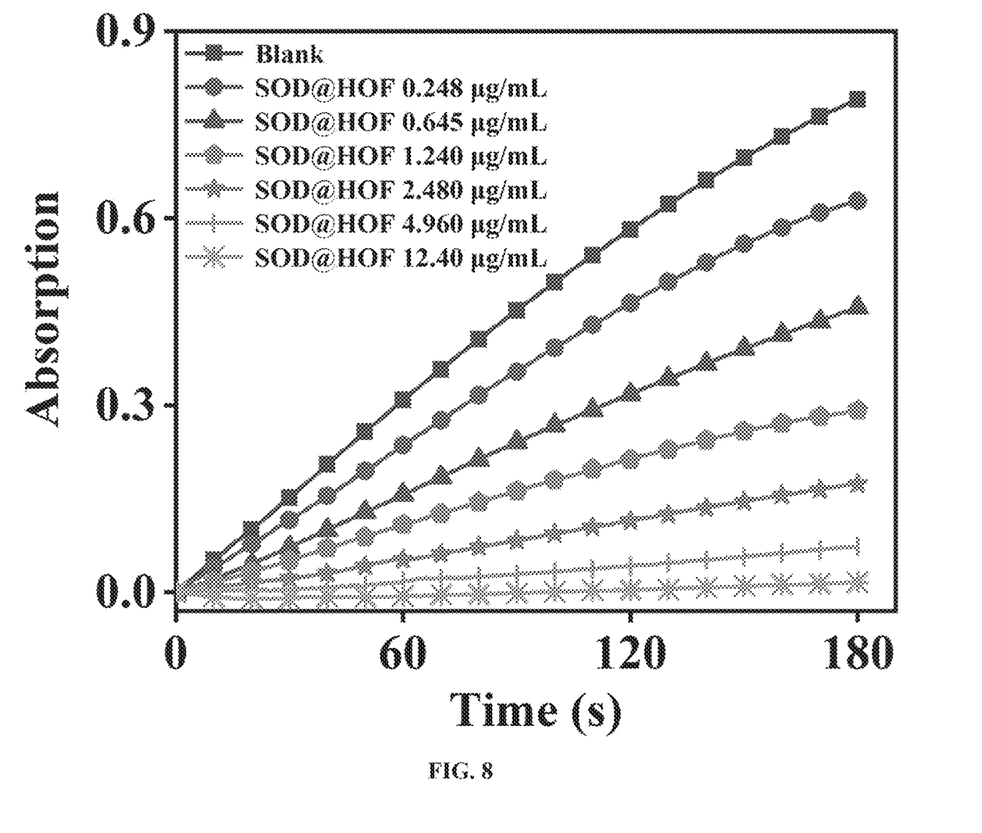
FIG. 8 is a result of a superoxide dismutase activity test in experimental test 3 of the present invention.

As shown in FIG. 8, with the increase in the concentration of antioxidant nanozymes, the oxidation inhibition rate of WST-8 was higher and higher, indicating that the scavenging effect of superoxide radicals was better and better, which proved that the antioxidant nanozymes had good superoxide dismutase activity, and the IC$_{50}$ value was 0.53 µg/mL.

Experimental Test 4

Figure 9:
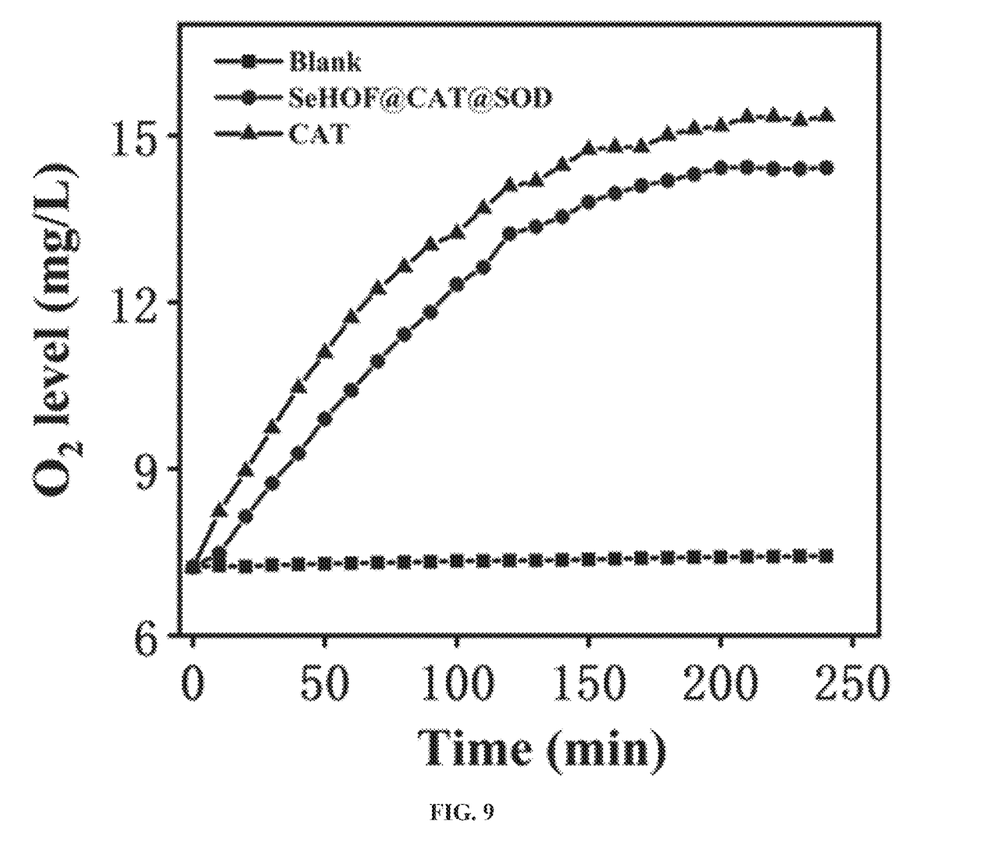
FIG. 9 is a result of a catalase activity test in experimental test 4 of the present invention.

The catalase activity of the multi-enzyme cascade antioxidant nanozyme prepared by embodiment 5 and embodiment 6 was tested, the method is as follows:

The catalase (CAT) mimic activity of antioxidant nanozymes was determined by monitoring the change of $O_2$ concentration by using a portable dissolved oxygen meter (JPB-607A, Leici China), all reactions were performed in 0.1 M of phosphate buffer (pH 7.4) at 25° C., and the results are shown in FIG. 9.

It can be seen from FIG. 9 that with the passage of time, the oxygen content in the solution is getting higher and higher, indicating that the antioxidant nanozyme can effectively decompose hydrogen peroxide into oxygen, which proves that the antioxidant nanozyme has good catalase activity.

Experimental Test 5

The cytotoxicity of the multi-enzyme cascade antioxidant nanozymes prepared by embodiments 4 to 6 was tested, the method is as follows:

Cell Counting Kit-8 (CCK-8) was used to quantitatively detect the effect of nanozymes on cell viability. PC12 cells were seeded in 96-well plates at a density of 5000 cells per well (total volume of 180 mL per well) for 24 h. Then, different concentrations of nanozymes (6.25 µg/mL, 12.5 µg/mL, 25 µg/mL, 50 µg/mL, and 100 µg/mL) were added to the cell culture medium. The cells were incubated with multi-enzyme cascade nanozymes for 24 h.

In order to determine the toxicity, 20 µL of CCK-8 solution was added to each well and the plate was incubated in a $CO_2$ incubator for 30 min. Then the solution is transferred from the 96-well plate to a new 96-well plate. Then the 96-well plate was rotated at room temperature for 30 s in the dark. The absorption value was measured at 450 nm by using a Bio-Rad 680 microplate reader. Cell viability was estimated according to the following equation: cell viability (%)=(OD treatment/OD control) 100%. The OD control was obtained in the absence of multi-enzyme cascade nanozymes, and the OD treatment was obtained in the presence of multi-enzyme cascade nanozymes. The results are shown in FIG. 10.

Figure 10:
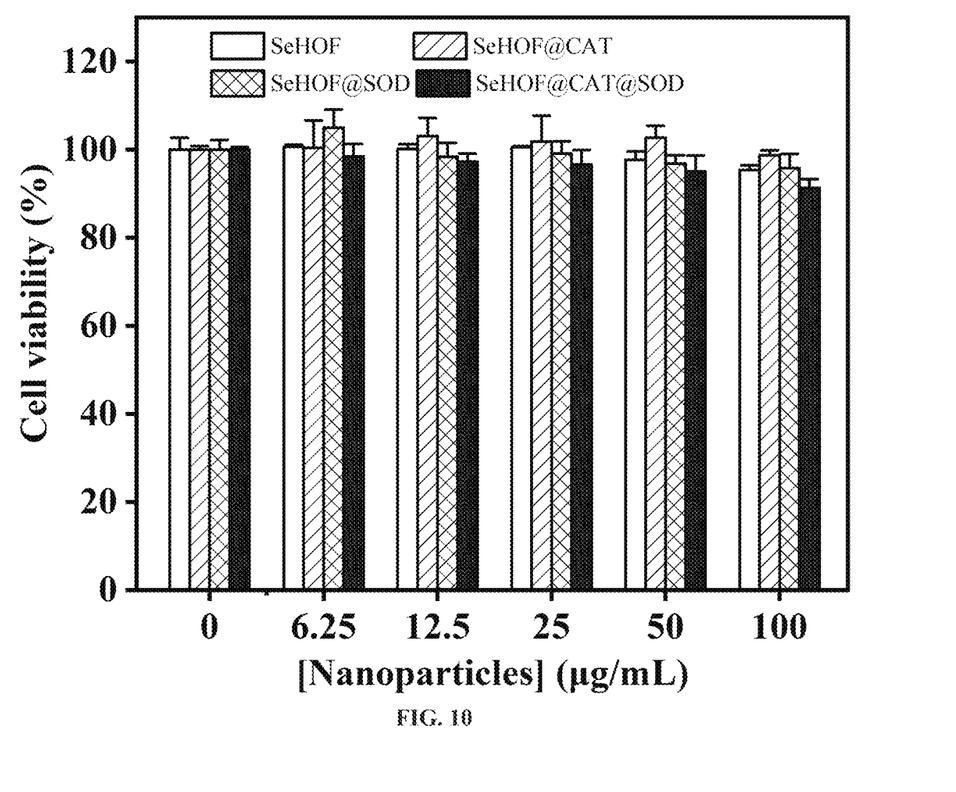
FIG. 10 is a result of a cytotoxicity test in experimental test 5 of the present invention.

It can be seen from FIG. 10 that the cell survival rate is above 90%, indicating that the multi-enzyme cascade nanozyme has good biocompatibility and is conducive to its biological application.

Experimental Test 6

The ROS scavenging capacity in vitro of multi-enzyme cascade antioxidant nanozymes prepared from embodiments 4 to 6 was tested, the method is as follows:

The production of ROS was monitored by using 2',7'-dichlorofluorescein diacetate (DCFH-DA), which reacts with intracellular free radicals and produces a fluorescent substance 2',7'-dichlorofluorescein (DCF). The intensity of DCF fluorescence is related to the level of ROS in cells. In order to carry out the experiment, 3T3 cells were inoculated in 6-well plates and incubated for 24 h. The cell culture medium was removed, and then the adherent cell PC12 was incubated with different nanozymes at 37° C. for 4 h. Before using, the adherent cell PC12 cells were washed three times with phosphate buffer saline (PBS) (pH 7.4) to remove the excess nanozymes. Then the cells were incubated with Rosup (50 μg·mL$^{-1}$) at 37° C. for 1 h.

After that, DCFH-DA solution was added to PC12 cells and the mixture was incubated at 37° C. for 1 h. Cells were collected and carried out the data acquisition and analysis on a flow cytometry. The excitation wavelength is 488 nm, and the signal is collected at channel 2 (500-560 nm). The results are shown in FIG. 11.

Figure 11:
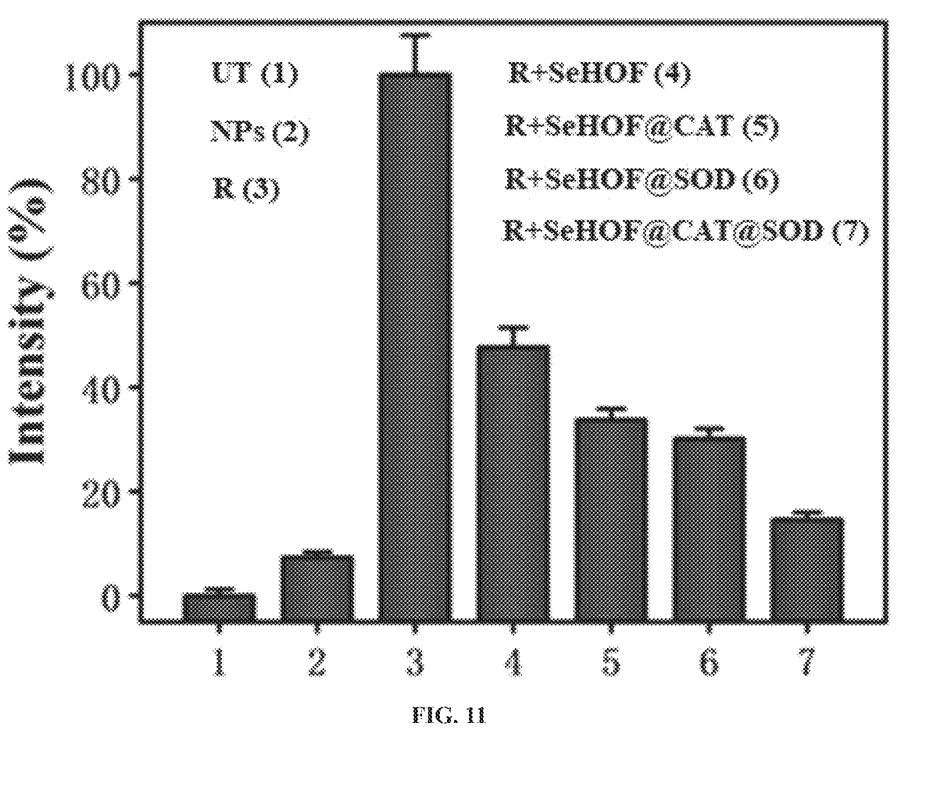
FIG. 11 is a result of ROS scavenging capacity in vitro in experimental test 6 of the present invention.

It can be seen from FIG. 11 that antioxidant nanozymes can effectively reduce the content of ROS in cells, and nano HOF loaded with superoxide dismutase and catalase showed the highest scavenging efficiency of ROS, with a scavenging rate of 88%, and showed the advantage of cascade antioxidant.

The present invention discloses a nano HOF based on selenium-containing ligand for the first time, the nano HOF does not contain metal and has good biocompatibility, which is a universal loading platform, and has high porosity, acid and alkali resistance and thermal stability, and is size-tunable, it can coat various types of enzymes at the same time, stabilize the conformation of the enzyme through the confinement effect, the high porosity can not only provide enough space for the enzyme, but also facilitate the transport of substances and the play of catalytic properties of the enzyme, 85-90% of the activity of the coated enzyme can be maintained; ROS can be effectively scavenged through the cascade catalysis between various enzymes, which provides a new idea for the construction of bio-friendly antioxidants and a new paradigm for the treatment of related diseases induced by continuous oxidative stress.

Finally, it should be noted that the above embodiments are merely used for describing the technical solutions of the present invention, rather than limiting the same. Although the present invention has been described in detail with reference to the preferred embodiments, those of ordinary skill in the art should understand that the technical solutions of the present invention may still be modified or equivalently replaced. However, these modifications or substitutions should not make the modified technical solutions deviate from the spirit and scope of the technical solutions of the present invention.

What is claimed is:

1. A nano hydrogen-bonded organic framework (HOF), wherein
   a morphology of the nano HOF is a rod-like structure, with a positive charge on a surface of the rod-like structure, and a size of the nano HOF is 10 μm-300 nm; the nano HOF is formed by reacting an amidine-containing compound and carboxyl groups of a selenium-containing ligand, wherein a structural formula of the amidine-containing compound is Formula (I), and a structural formula of the selenium-containing ligand is Formula (II), wherein R of the Formula (II) is one of H—, F—, Br—, OH—, and —CH$_3$.

2. A method for preparing an antioxidant nanozyme comprising a step of adding the nano HOF according to claim 1 to an enzyme, wherein the nano HOF is a loading platform, and the enzyme is an antioxidant enzyme.

3. A multi-enzyme cascade antioxidant nanozyme comprising the nano HOF according to claim 1 and an antioxidant enzyme.

4. A method for reducing a concentration of reactive oxygen species (ROS) in cells comprising a step of adding the multi-enzyme cascade antioxidant nanozyme according to claim 3 to a cell.

5. The multi-enzyme cascade antioxidant nanozyme according to claim 3, wherein the enzyme is one or two of glutathione peroxidase, catalase, or superoxide dismutase.

* * * * *